United States Patent
Kourai et al.

(10) Patent No.: US 6,664,224 B2
(45) Date of Patent: Dec. 16, 2003

(54) QUATERNARY AMMONIUM SALT AND PROCESS FOR THE PREPARATION THEREOF

(75) Inventors: Hiroki Kourai, Tokushima (JP); Shigeyuki Shibata, Aichi (JP); Katsuyoshi Harada, Aichi (JP); Masayoshi Kume, Aichi (JP)

(73) Assignee: Toagosei Co., Ltd., Tokyo (JP)

( * ) Notice: Subject to any disclaimer, the term of this patent is extended or adjusted under 35 U.S.C. 154(b) by 387 days.

(21) Appl. No.: 09/854,668

(22) Filed: May 15, 2001

(65) Prior Publication Data

US 2002/0006888 A1 Jan. 17, 2002

(30) Foreign Application Priority Data

May 15, 2000 (JP) .................................... P. 2000-141352
Feb. 1, 2001 (JP) .................................... P. 2001-026173

(51) Int. Cl.$^7$ ................................................. C11D 3/48
(52) U.S. Cl. ....................... 510/384; 510/112; 510/382; 510/391; 564/281; 564/282; 564/290; 564/305
(58) Field of Search .................................. 510/112, 382, 510/384, 391; 564/281, 282, 290, 305

(56) References Cited

FOREIGN PATENT DOCUMENTS

| EP | 0 825 175 A1 | 2/1998 |
|---|---|---|
| EP | 825175 | * 2/1998 |
| JP | A-6-321902 | 11/1994 |
| JP | A-10-114604 | 5/1998 |
| JP | A-2000-95763 | 4/2000 |

OTHER PUBLICATIONS

European Search Report dated Sep. 17, 2001.

* cited by examiner

*Primary Examiner*—Charles Boyer
(74) *Attorney, Agent, or Firm*—Sughrue Mion, PLLC

(57) ABSTRACT

The novel quaternary ammonium salt according to the invention has two quaternary ammonium groups connected to a benzene ring, wherein two $C_{4-12}$ alkyl groups and one $C_{1-2}$ alkyl group are connected per one nitrogen atom constituting the quaternary ammonium. The compound is used as an antimicrobial agent, exhibits a high safety to human as compared with known antimicrobial agents, exerts an excellent sterilizing effect itself and exhibits a wide sterilizing spectrum. In particular, the compound is used as a presevative for eye drop.

11 Claims, No Drawings

QUATERNARY AMMONIUM SALT AND PROCESS FOR THE PREPARATION THEREOF

FIELD OF THE INVENTION

The present invention relates to a novel quaternary ammonium salt and a process for the preparation thereof. The compound according to the present invention is useful as an antimicrobial agent such as preservative for eye drop.

BACKGROUND OF THE INVENTION

A quaternary ammonium salt having an antimicrobial activity has long been known and is now widely used. However, conventional quaternary ammonium salts are normally disadvantageous in that they show deteriorated sterilizing power and antimicrobial power due to the effect of saccharides, protein and lipid or in an acid range having a low pH value and have no effect on cellular spore.

As solutions to the foregoing problems, a compound having two structural units called quaternary ammonium per molecular has been proposed, which unit is capable of having four alkyl groups or other groups connected to one nitrogen atom, e.g., the antimicrobial agent comprising quaternary ammonium salt in JP-A-6-321902 (The term "JP-A" as used herein means an "unexamined published Japanese patent application") and JP-A-10-114604. The compound disclosed in these published applications has methyl or ethyl groups connected thereto in a proportion of 2 or more per one of nitrogen atoms constituting the quaternary ammonium. Accordingly, this compound has a high antimicrobial activity and thus is a good compound from the standpoint of antimicrobial properties. This compound has been actually used as an antimicrobial agent. This compound has a high antimicrobial activity but it has been desired to improve the safety of this compound to human.

SUMMARY OF THE INVENTION

It is therefore an object of the present invention to provide a novel compound which exhibits a high antimicrobial activity and a wide antimicrobial spectrum and can be used as an antimicrobial agent having a high safety to human.

The other objects of the present invention will become apparent from the following detailed description and examples.

The present invention lies in a quaternary ammonium salt represented by the following general formula (1):

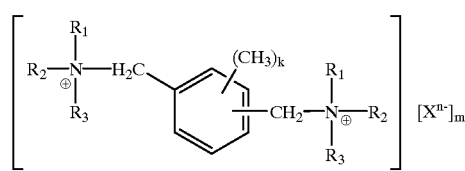

wherein $R_1$ and $R_2$ each represent a $C_{4-12}$ alkyl group and may be the same or different; $R_3$ represents a $C_{1-2}$ alkyl group; k represents an integer of from 0 to 4; X represents an inorganic or organic anion group; n represents the valence of the anion group X which is selected from 1 and 2; and m represents an integer of 2 when n is 1 or 1 when n is 2.

The compound of the invention can be obtained by the following reaction [I], [II] or [III]:

Reaction [I]

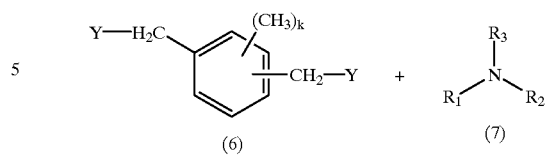

In the general formula (6), k represents an integer of from 0 to 4, and Y represents a chlorine atom, bromine atom or iodine atom.

In the general formula (7), $R_1$ and $R_2$ each represent a $C_{4-12}$ alkyl group, and $R_3$ represents a $C_{1-2}$ alkyl group.

Reaction [II]

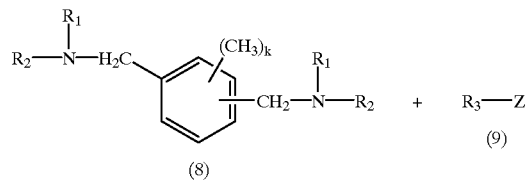

In the general formula (8), $R_1$ and $R_2$ may be the same or different and each represent a $C_{4-12}$ alkyl group, and k represents an integer of from 0 to 4.

In the general formula (9), $R_3$ represents a $C_{1-2}$ alkyl group, and Z represents a chlorine atom, bromine atom, iodine atom or a group represented by any one of the following general formulae (10) and (11):

wherein $R_6$ represents a $C_{1-2}$ alkyl group; and

wherein $R_7$ and $R_8$ each represent a hydrogen atom, $C_{1-2}$ alkyl group or carboxyl group.

Reaction [III]:

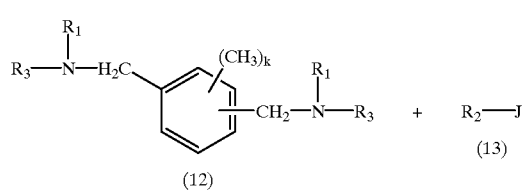

In the general formula (12) $R_1$ represents a $C_{4-12}$ alkyl group, $R_3$ represents a $C_{1-2}$ alkyl group, and k represents an integer of from 0 to 4.

In the general formula (13), $R_2$ represents a $C_{4-12}$ alkyl group; and J represents a chlorine atom, bromine atom, iodine atom or a group represented by the general formula (11).

DETAILED DESCRIPTION OF THE INVENTION

A. Novel Compound

The present invention relates to a novel quaternary ammonium salt represented by the following general formula (1):

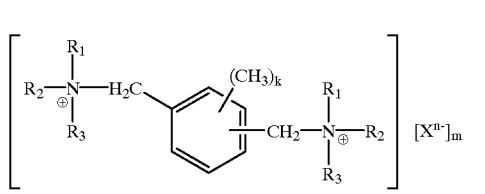

(1)

wherein $R_1$ and $R_2$ each represent a $C_{4-12}$ alkyl group and may be the same or different; $R_3$ represents a $C_{1-2}$ alkyl group; k represents an integer of from 0 to 4; X represents an inorganic or organic anion group; n represents the valence of the anion group X which is selected from 1 and 2; and m represents an integer of 2 when n is 1 or 1 when n is 2.

In the general formula (1), the alkyl group represented by $R_1$ or $R_2$ there may be used an alkyl group having from 4 to 12 carbon atoms. In order to balance between antimicrobial properties and safety to human, the number of carbon atoms in the alkyl group is preferably from 5 to 10, more preferably from 6 to 8. $R_3$ may be either methyl or ethyl but is preferably methyl to exhibit higher antimicrobial properties.

In the general formula (1), X represents an inorganic or organic anion group. Preferred examples of such an inorganic or organic anion group include iodine ion, bromine ion, chlorine ion, fluorine ion, iodic acid ion, bromic acid ion, chloric acid ion, periodic acid ion, perchloric acid ion, chlorous acid ion, hypochlorous acid ion, nitric acid ion, nitrous acid ion, sulfuric acid ion, hydroxyl group ion or an anion group represented by any one of the following general formulae (2) to (5).

The number (m) of anion groups X connected to the compound of the general formula (1) is such that the product of n and m is 2 wherein n is the valence of the anion group X. For example, when the valence of the anion group X is −2, m is 1. When the valence of the anion group X is −1, m is 2.

  (2)

wherein $R_4$ represents a $C_{1-7}$ alkyl or alkenyl group which may have one or more hydroxyl group or carbonyl group;

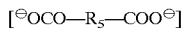  (3)

wherein $R_5$ does not exist (the two groups COO are directly bonded to each other) or represents a $C_{1-8}$ alkyl or alkenyl group which may have one or more hydroxyl group;

  (4)

wherein $R_6$ represents a $C_{1-2}$ alkyl group; and

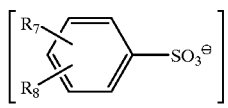  (5)

wherein $R_7$ and $R_8$ each represent a hydrogen atom, $C_{1-12}$ alkyl group or carboxyl group.

B. Process for the Preparation of Novel Compound

The quaternary ammonium salt represented by the general formula (1) can be prepared by any one of the following processes.

B-1. First-class Preparation Process

The first embodiment of the process for the preparation of the quaternary ammonium salt represented by the general formula (1) involves the reaction of a halogen compound represented by the following general formula (6) with a tertiary amine represented by the following general formula (7):

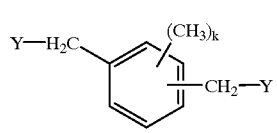

(6)

wherein k represents an integer of from 0 to 4; and Y represents a chlorine atom, chlorine atom or iodine atom; and

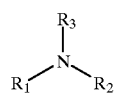

(7)

wherein $R_1$ and $R_2$ each represent a $C_{4-12}$ alkyl group; and $R_3$ represents a $C_{1-2}$ alkyl group.

Examples of the compound represented by the general formula (6) include halogen compounds such as α, α'-dichloro-o-xylene, α, α'-dichloro-m-xylene, α, α'-dichloro-p-xylene, α, α'-dibromo-o-xylene, α, α'-diiodo-m-xylene, 3,6-bis(chloromethyl)durene, 2,4-bis(chlorometh)-dimethylbenzene and 2,5-bis(chloromethyl) toluene.

Examples of the compound represented by the general formula (7) include tertiary amines such as N,N-dipentyl-N-methylamine, N,N-dihexyl-N-methylamine, N,N-diheptyl-N-methylamine, N-butyl-N-hexyl-N-methylamine, N-pentyl-N-hexyl-N-methylamine, N-hexyl-N-octyl-N-methylamine, N,N-dipentyl-N-ethylamine, N,N-dihexyl-N-ethylamine and N-pentyl-N-hexyl-N-ethylamine.

These reactions can be effected at a temperature of from 50° C. to 120° C. in a proper organic solvent. The proportion of the tertiary amine of the general formula (7) to the halogen compound of the general formula (6) may be not less than 2 mols, e.g., from 2.0 to 2.3 mols per mol of the compound of the general formula (6).

As a reaction solvent there may be used an alcohol such as methanol, ethanol and n-propanol, mixture of water and alcohol or aromatic organic solvent such as benzene, toluene and xylene. The reaction temperature may be not lower than 80° C. At this reaction temperature, the reaction can be normally completed in 1 to 40 hours.

B-2. Second-class Preparation Process

The second embodiment of the process for the preparation of the quaternary ammonium salt represented by the general formula (1) involves the reaction of a tertiary amine represented by the following general formula (8) with a quaterizing agent represented by the following general formula (9):

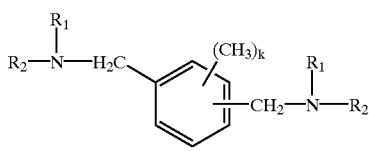
(8)

wherein $R_1$ and $R_2$ may be the same or different and each represent a $C_{4-12}$ alkyl group; and k represents an integer of from 0 to 4; and $$R_3—Z \qquad (9)$$

wherein $R_3$ represents a $C_{1-2}$ alkyl group; and Z represents a chlorine atom, bromine atom, iodine atom or a group represented by any one of the following general formulae (10) and (11):

(10)

wherein $R_6$ represents a $C_{1-2}$ alkyl group; and

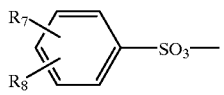
(11)

wherein $R_7$ and $R_8$ each represent a hydrogen atom, $C_{1-12}$ alkyl group or carboxyl group.

Examples of the compound of the general formula (8) include N,N,N',N'-tetrapentyl-o-xylylenediamine, N,N'-dibutyl-N,N'-dihexyl-o-xylylenediamine, N,N,N',N'-tetrahexyl-m-xylylenediamine, N,N,N',N'-tetraheptyl-p-xlylenediamine, N,N,N',N'-tetrahexyl-2,3,5,6-tetramethyl-p-xylylenediamine, N,N'-dibutyl-N,N'-dihexyl-2,3,5,6-tetramethyl-p-xylylenediamine, N,N'-dihexyl-N,N'-dioctyl-2,3,5,6-tetramethyl-p-xylylenediamine, N,N,N',N'-tetrapentyl-1,3,5-trimethyl-m-xylylenediamine, N,N,N',N'-tetrahexyl-2,4-dimethyl-p-xylylenediamine, and N,N,N',N'-tetrahexyl-2-methyl-p-xylylenediamine.

Examples of the compound represented by the general formula (9) include halogenated alkyl such as methane chloride, ethane chloride, methane bromide, ethane bromide and methane iodide, dialkylsulfuric acid such as dimethylsulfuric acid, and sulfonic acid alkyl such as methyl p-toluenesulfonate.

These reactions can be conducted at a temperature of from 50° C. to 120° C. in a proper solvent. Many quaterizing agents are inactivated when acted upon by heat or the like. The quaterizing agent compound represented by the general formula (9) is preferably used in excess with the tertiary amine represented by the general formula (8), i.e., not lower than 4 mols, more preferably not lower than 6 mols per mol of the tertiary amine represented by the general formula (8).

Examples of the reaction solvent employable herein include alcohol such as methanol, ethanol, n-propanol and 2-methoxy-ethanol, and mixture of water and alcohol. Further examples of the reaction solvent include aprotic solvent such as N,N-dimethylformamide, N-methylformamide, nitromethane, nitroethane, and acetonitrile.

Referring to the reaction atmosphere, synthesis can be made in the atmosphere. However, the reaction is preferably effected in a nitrogen atmosphere. The reaction temperature may be not lower than 80° C. At this temperature, the reaction can be normally completed in 1 to 40 hours.

The foregoing reaction may also be effected at a temperature of from 50° C. to 100° C. under pressure, preferably from 10 to 100 MPa (megapascal) in a proper solvent in an autoclave. The reaction time may be normally from 5 hours to 120 hours.

The tertiary amine of the general formula (8) can be obtained, e.g, by the reaction of the halogen compound of the general formula (6) with a compound represented by the following general formula (15):

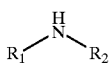
(15)

wherein $R_1$ and $R_2$ each represent a $C_{4-12}$ alkyl group.

Examples of the compound of the general formula (15) include secondary amines such as N,N-dipentylamine, N,N-dihexylamine, N-butyl-N-hexylamine and N-butyl-N-octylamine.

The tertiarization reaction of the compound of the general formula (6) with the compound of the general formula (15) may be effected at a temperature of from 50° C. to 120° C. in a proper organic solvent such as alcohol, mixture of alcohol and water and aromatic organic solvent for 1 hour to 48 hours. The proportion of the secondary amine of the general formula (15) in the halogen compound of the general formula (6) is preferably 4 to 6 mols, particularly from 4.1 to 4.4 mols per mol of the compound of the general formula (6). As a result of the foregoing tertiarization reaction, a tertiary amine and a hydrochloride of amine are produced as a desired intermediate product and a by-product which is used as a starting material, respectively.

The separation of the tertiary amine as a desired intermediate product and the hydrochloride of amine as a starting material may be carried out by any method such as extraction. Further, the separation of the tertiary amine and the hydrochloride of amine can be easily accomplished by the use of the difference in solubility between organic solvents.

The hydrochloride of amine as a by-product can be regenerated to a starting material amine. When the hydrochloride of amine as a by-product is acted upon by a base such as aqueous solution of NaOH, a water-insoluble organic phase is produced. When the organic phase is subjected to ordinary separation/purification, a secondary amine is obtained as a starting material. The secondary amine thus obtained can be again used as a starting material.

B-3. Third-class Preparation Process

The third embodiment of the process enabling the preparation of the quaternary ammonium salt represented by the general formula (1) involves the treatment of a tertiary amine represented by the following general formula (12) with a quaterizing agent represented by the following general formula (13):

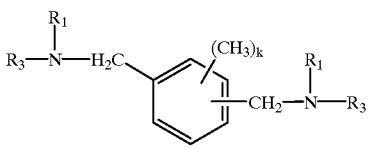
(12)

wherein $R_1$ represents a $C_{4-12}$ alkyl group; $R_3$ represents a $C_{1-2}$ alkyl group; and k represents an integer of from 0 to 4.

$$R_2\text{—J} \qquad (13)$$

wherein $R_2$ represents a $C_{4-12}$ alkyl group; and J represents a chlorine atom, bromine atom, iodine atom or a group represented by the general formula (11).

Examples of the compound represented by the general formula (12) include N,N'-dipentyl-N,N'-dimethyl-o-xylylenediamine, N,N'-dihexyl-N,N'-dimethyl-o-xylylene diamine, N,N'-dipentyl-N,N'-diethyl-o-xylylenediamine, N,N'-dipentyl-N,N'-dimethyl-m-xylylenediamine, N,N'-dipentyl-N,N'-dimethyl-p-xylylenediamine, N,N'-dihexyl-N,N'-dimethyl-2,3,5,6-tetramethyl-p-xylylenediamine, N,N'-dipentyl-N,N'-dimethyl-1,3,5-timethyl-m-xylylenediamine, and N,N'-dihexyl-N,N'-dimethyl-2,4-dimethyl-p-xylylenediamine.

Examples of the compound represented by the general formula (13) include halogenated alkyl such as butane chloride, pentane chloride, hexane chloride, decane chloride, nonane bromide, decane bromide, pentane iodide and heptane iodide, and sulfonic acid alkyl such as butyl p-toluenesulfonate, pentyl p-toluenesulfonate, hexane p-toluenesulfonate and dodecane p-toluenesulfonate.

The reaction of the compound of the general formula (12) with the compound of the general formula (13) can be effected substantially according to the second preparation process. In some detail, as a solvent there may be preferably used an alcohol, mixture of water and alcohol or aprotic solvent such as N,N-dimethylformamide and methyl cellosolve. The reaction can be effected in the absence of solvent. The reaction atmosphere, reaction temperature and reaction time may be the same as used in the second preparation process. The proportion of the quaterizing agent of the general formula (13) in the tertiary amine of the general formula (12) may be not smaller than 2 mols, e.g., from 2.0 to 2.3 mols per mol of the compound of the general formula (12). The foregoing reaction can proceed in the presence of a proper solvent under pressure in an autoclave in the same manner as in the second reaction.

The tertiary amine represented by the general formula (12) can be obtained by the reaction of the halogen compound represented by the general formula (6) with a compound represented by the following general formula (16):

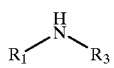

(16)

wherein $R_1$ represents a $C_{4-12}$ alkyl group; and $R_3$ represents a $C_{1-2}$ alkyl group.

Examples of the compound represented by the general formula (16) include secondary amines such as N-pentyl-N-methylamine, N-hexyl-N-methylamine and N-hexyl-N-ethylamine.

The tertiarization reaction of the compound represented by the general formula (6) with the compound represented by the general formula (16) can be effected at a temperature of from 50° C. to 120° C. in a proper organic solvent such as alcohol, mixture of water and alcohol and aromatic organic solvent for 1 hour to 48 hours substantially according to the reaction of the compound represented by the general formula (6) with the compound represented by the general formula (15). The proportion of the secondary amine represented by the general formula (16) in the halogen compound represented by the general formula (6) is preferably from 4 to 6 mols, particularly from 4.1 to 4.4 mols per mol of the compound of the general formula (6). The separation of the tertiary amine as a desired intermediate product and the hydrochloride of amine as a starting material and the regeneration of the starting material amine hydrochloride as a by-product can be effected substantially according to the reaction of the compound represented by the general formula (6) with the compound represented by the general formula (15).

B-4. Process for the Purification of Compound

The compound produced by the foregoing third preparation process can be easily purified by an ordinary separation/purification method such as column chromatographic separation and recrystallization as necessary.

B-5. Exchange of Anion Group

The quaternary ammonium salt prepared by the foregoing third preparation process can be subjected to ion exchange to exchange the anion group incorporated therewith with another specific anion group. The ion exchange can be easily carried out by treating the quaternary ammonium salt in a column filled with an anion exchange resin.

In some detail, the quaternary ammonium salt of the invention comprises as a cation group a quaternary ammonium salt represented by the following general formula (14) incorporated therein. The anion as the counter ion of such a cation group there may be prepared by effecting ion exchange so that the anion group synthesized by any one the foregoing three preparation processes is replaced by an iodine ion ($I^-$), bromine ion ($Br^-$), chlorine ion ($Cl^-$), iodic acid ion ($IO_3^-$), bromic acid ion ($BrO_3^-$), chloric acid ion ($ClO_3^-$), periodic acid ion ($IO_4^-$), erchloric acid ion ($ClO_4^-$), chlorous acid ion ($ClO_2^-$), hypochlorous acid ion ($ClO^-$), nitric acid ion ($NO_3^-$), nitrous acid ion ($NO_2^-$), sulfuric acid ion ($SO_4^{2-}$), hydroxyl group ion ($OH^-$) or an anion group represented by any one of the following general formulae (2) to (5):

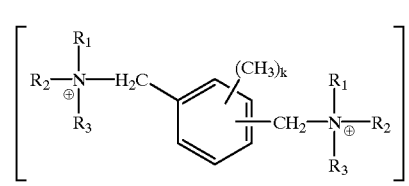

(14)

wherein $R_1$ and $R_2$ each represent a $C_{4-12}$ alkyl group and may be the same or different; $R_3$ represents a $C_{1-2}$ alkyl group; and k represents an integer of from 0 to 4.

C. Antimicrobial Properties

The compound of the invention represented by the general formula (1) thus obtained exhibits a wide antimicrobial spectrum against various bacteria and fungi as described later in Test Examples 1 and 2.

The compound of the invention represented by the general formula (1) exhibits a particularly strong sterilizing activity when the alkyl chain ($R_1$, $R_2$) has from 5 to 10, particularly from 6 to 8 carbon atoms.

The compound of the invention represented by the general formula (1) exhibits an excellent sterilizing activity, i.e., minimum sterilizing concentration of from $\frac{1}{10}$ to $\frac{1}{100}$ of that of conventional commercial quaternary ammonium salts. Accordingly, the compound of the invention represented by the general formula (1) can exert a sterilizing effect equal to that of the conventional commercial sterilizers of the same kind when used in an amount far less than that of the conventional sterilizers.

D. Safety of Compound

The quaternary ammonium salt of the invention is a compound having an extremely high safety, i.e., $LD_{50}$ (rat) of not smaller than 2,000 mg/kg in oral toxicity test on rat.

Further, the compound of the invention represented by the general formula (1) was determined for hemolytic activity. As a result, the compound of the invention represented by the general formula (1) was found to have a hemolytic activity of 10 times or more lower than that of conventional quaternary ammonium salts such as benzalkonium chloride and those proposed in JP-A-6-321902 and JP-A-10-114604. Thus, the compound of the invention represented by the general formula (1) exhibits an extremely low toxicity to human being.

E. Usage of Compound

The compound according to the invention can be used as an antimicrobial agent in a wide range of arts such as antimicrobial deodorized fiber product, leather product, building material, coating compound, adhesive, plastic, film, paper, pulp, metal working oil, food, pharmaceuticals, medical and atmospheric infectants, eye drop, detergent, cosmetics, stationary product, agricultural chemicals, stock farming, etc.

The compound according to the invention can exhibit an antimicrobial effect without any supplemental ingredient or with solid or liquid carrier. Depending on the situation, surface-active agent, other ingredient, etc. can be mixed to form emulsion, hydrate agent, granular agent, powder, spray agent or aerosol.

The proportion of the compound of the invention is normally from 0.0001 to 100% by weight, preferably from 0.001 to 10% by weight on the total amount of antimicrobial agent.

F. Use as Preservative for Eye Drop

Examples of conventional preservatives for eye drop include compounds having cation group such as quaternary ammonium salt and guanidine, alcohols, aminobenzoic acid ester, and sorbic acid. Quaternary ammonium salts, particularly benzalkonium chloride, are commonly used because they have a great anti-septic power.

However, when these preservatives are incorporated in an eye drop, the resulting eye drop can become slightly turbid depending on the kind of other compounds to be incorporated as pharmaceutical components. It has been reported that when benzalkonium chloride is incorporated in an amount of not smaller than 0.01%, the cornea is damaged. Thus, the amount of benzalkonium chloride to be incorporated in an eye drop is restricted to a value at which no safety problem occurs.

Thus, when the conventional preservatives are incorporated in an eye drop in a low concentration, no turbidity occurs. However, the resulting anti-septic effect is insufficient. Accordingly, various improvement techniques for enhancing anti-septic effect or preventing turbidity have been proposed as in JP-A-2-311417 and JP-A-6-40910.

The inventors made extensive studies. As a result, it was found that the compound of the invention represented by the general formula (1) (hereinafter abbreviated as "compound (1)of the invention") is extremely effective as a preservative for providing a transparent eye drop without producing insoluble materials with various compounds used as effective components for eye drop as described later in Test Example 1.

In other words, the preservative for eye drop according to the invention comprises as an effective component the compound (1) of the invention incorporated therein.

Examples of eye drop pharmaceutical compounds which cause no turbidity even when mixed with the compound (1) of the invention include compounds having carboxyl group such as sodium hyaluronate, dipotassium glycyrrhizinate, pyrenoxin, lysozyme chloride, sodium cromoglicate and carboxy vinyl polymer, compounds having sulfonic acid group such as chondroitin sodium sulfate, sodium dimethylisopropylazulene sulfonate, sodium colistinmethanesulfonate and dexamethasone sodium metasulfobenzoate, compounds having phosphonyl group such as flavin-adenine dinucleotide, and pilocarpine hydrochloride. All these compounds have not heretofore been able to be incorporated as pharmaceutical components because they cause turbidity when mixed with benzalkonium chloride.

The anti-septic effect of the preservative for eye drop according to the invention cannot be adversely affected by various components which are optionally incorporated in an eye drop in addition to the foregoing pharmaceutical components, e.g., effective component such as antiphlogistic, vitamin and antihistamines, additives such as pH adjustor, buffer, isotonic agent and solubilizer.

Further, the compound (1) of the invention exhibits a wide sterilizing spectrum against various bacteria and fungi as well as a high sterilizing activity and anti-septic power as compared with benzalkonium chloride, which is a conventional commonly used quaternary ammonium salt, as described later in Test Examples 3 to 5.

The proportion of the compound (1) of the invention in an eye drop is normally from 0.0005 to 0.1% by weight, preferably from 0.002 to 0.02% by weight based on the total amount of the eye drop. When the proportion of the compound (1) of the invention in an eye drop falls below 0.0005% by weight, the anti-septic effect of the preservative may become insufficient. On the contrary, when the proportion of the compound (1) of the invention in an eye drop exceeds 0.1% by weight, it may be economically disadvantageous.

G. The present invention will be further described in the following Examples and Comparative Examples, but the present invention should not be construed as being limited thereto.

G-1: SYNTHESIS EXAMPLES

Examples of the synthesis of the compound of the invention will be described hereinafter.

Compounds thus synthesized will be hereinafter abbreviated as "$x_1$-BAM$X_2$-$x_3x_4$" (in which $x_1$ represents a number indicating the bonding position in the benzene ring in the quaternary ammonium salt (ortho position: 2; meta position: 3; para position: 4), $x_2$ represents a symbol corresponding to the value of k in the general formula (1) (0: p; 3: T; 4: D), $x_3$ represents a number of from 4 to 12 indicating the number of carbon atoms contained in the long alkyl group connected to the quaternary ammonium salt, and $x_4$ represents a symbol corresponding to the kind of anion (chlorine: C; bromine: B; iodine: I; sulfate: S).

Example 1

In a 300 ml reaction vessel were charged 20 mmol of α,α'-dichloro-p-xylene as a halogen compound, 42 mmol of N,N-dihexyl-N-methylamine as a tertiary amine and 100 ml of ethanol as a solvent. The reaction mixture was then allowed to undergo reaction by heating under reflux for 5 hours. Ethanol as a solvent was then removed from the reaction product under reduced pressure to obtain a crude crystal. The crude crystal was recrystallized from diethyl ether, and then dried under reduced pressure to obtain 8.02 g of 1,4-bis(N,N-dihexyl-N-methylammoniomethyl)

phenylene dichloride (abbreviated as 4BAMP-6C) in the form of white compound. The yield of the desired compound was 70%.

The results of $^1$H-NMR analysis (solvent: $CD_3OD$) of 4BAMP-6C thus obtained will be given below (hereinafter, unit will be δ ppm).
0.94 (12H, t, J=6.8 Hz), 1.40 (24H, s), 1.85 (8H, br s), 3.02 (6H, s), 3.31 (8H, m), 4.62 (4H, s), 7.71 (4H, s)

The results of elementary analysis for $C_{34}H_{66}N_2Cl_2$ will be given below.

|  | C | H | N |
|---|---|---|---|
| Calculated %: | 71.17 | 11.59 | 4.88 |
| Found %: | 71.10 | 11.41 | 5.13 |

From these results of analysis, the product obtained was identified as the desired compound.

The sample 4BAMP-6C thus obtained was then determined for oral toxicity ($LD_{50}$: rat). The results were greater than 2,000 mg/kg.

Example 2

The procedure of Example 1 was followed except that, as the tertiary amine, N,N-dioctyl-N-methylamine was used instead of N,N-dihexyl-N-methylamine. As a result, 7.10 g of 1,4-bis(N,N-dioctyl-N-methylammoniomethyl)phenylene dichloride (abbreviated as "14BAMP-8C") was obtained as the desired compound in the form of white compound. The yield of the desired compound was 52%.

The results of $^1$H-NMR analysis (solvent: $CD_3OD$) of 4BAMP-8C thus obtained will be given below.
0.91 (12H, t, J=7.2 Hz), 1.38 (40H, s), 1.85 (8H, br s), 3.05 (6H, s), 3.31 (8H, m), 4.68 (4H, s), 7.74 (4H, s)

The results of elementary analysis for $C_{42}H_{82}N_2Cl_2$ will be given below.

|  | C | H | N |
|---|---|---|---|
| Calculated %: | 73.53 | 12.05 | 4.08 |
| Found %: | 73.38 | 12.01 | 4.46 |

From these results of analysis, the product obtained was identified as the desired compound.

Example 3

The procedure of Example 1 was followed except that, as the halogen compound, α,α'-dichloro-m-xylene was used instead of α,α'-dichloro-p-xylene. As a result, a white crude crystal was obtained. This crude crystal was highly hygroscopic and thus immediately became liquid. The crude product was washed with hexane, and then dried under reduced pressure to obtain 12.21 g of 1,3-bis(N,N-dihexyl-N-methylammoniomethyl)phenylene dichloride (abbreviated as "3BAMP-6C") as the desired compound in the form of white compound. The yield of the desired compound was 89%.

The results of $^1$H-NMR analysis (solvent: $CD_3OD$) of 3BAMP-6C thus obtained will be given below.
0.91 (12H, t, J=6.4 Hz), 1.38 (40H, s), 1.85 (8H, br s), 3.05 (6H, s), 3.31 (8H, m), 4.68 (4H, s), 7.50 (1H, m), 7.71 (2H, m), 7.68 (1H, m)

These results show that 3BAMP-6C is the desired compound.

Example 4

The procedure of Example 1 was followed except that, as the halogen compound, α,α'-dichloro-o-xylene was used instead of α,α'-dichloro-p-xylene. As a result, a light yellow liquid was obtained. This liquid was washed with hexane, and then dried under reduced pressure to obtain 11.84 g of 1,2-bis(N,N-dihexyl-N-methylammoniomethyl)phenylene dichloride (abbreviated as "2BAMP-6C") as the desired compound in the form of white liquid compound. The yield of the desired compound was 89%.

The results of $^1$H-NMR analysis (solvent: $CD_3OD$) of 2BAMP-6C thus obtained will be given below.
0.91 (12H, t, J=6.8 Hz), 1.38 (40H, s), 1.85 (8H, br s), 3.05 (6H, s), 3.31 (8H, m), 4.68 (4H, s), 7.52 (2H, m), 7.72 (2H, m)

These results show that 2BAMP-6C is the desired compound.

Example 5

In a 300 ml reaction vessel were charged 20 mmol of N,N,N',N'-tetrapentyl-p-xylylenediamaine as a tertiary amine, 120 mmol of methyl p-toluenesulfonate as a quaterizing agent and 100 g of ethanol as a solvent. The reaction mixture was then allowed to undergo reaction by heating under reflux in a nitrogen atmosphere for 5 hours. Ethanol as a solvent was then removed from the reaction product. The reaction product was then washed with water and ether. The solvent was then removed under reduced pressure. The resulting solid was recrystallized from acetonitrile, and then dried under reduced pressure to obtain 10.79 g of 1,4-bis(N,N-dipentyl-N-methylammoniomethyl)phenylene di-p-tolyenesulfonate (abbreviated as 4BAMP-5S) as the desired compound in the form of white solid compound. The yield of the desired compound was 68%.

The results of $^1$H-NMR analysis (solvent: $CD_3OD$) of 4BAMP-5S thus obtained will be given below.
0.94 (12H, t, J=7.2 Hz), 1.36 (16H, s), 1.81 (8H, br s), 2.37 (6H, s), 2.98 (6H, s), 3.13 (8H, m), 4.44 (4H, s), 7.23 (4H, d, J=7.6 Hz), 7.70 (8H, s+d, J=5.6 Hz)

The results of elementary analysis for $C_{44}H_{72}N_2S_2O_6$ will be given below.

|  | C | H | N |
|---|---|---|---|
| Calculated %: | 66.97 | 9.20 | 3.55 |
| Found %: | 66.84 | 9.14 | 4.15 |

These results of analysis show that 4BAMP-5S is the desired compound.

Example 6

The procedure of Example 5 was followed except that, as the tertiary amine, N,N,N',N'-tetrahexyl-p-xylylenediamine was used instead of N,N,N',N'-tetrapentyl-p-xylylenediamine. As a result, 12.63 g of 1,4-bis(N,N-dihexyl-N-methylammoniomethyl)phenylene di-p-toluenesulfonate (abbreviated as "4BAMP-6S") was obtained as the desired compound in the form of white solid compound. The yield of the desired compound was 75%.

The results of $^1$H-NMR analysis (solvent: $CD_3OD$) of 4BAMP-6S thus obtained will be given below.
0.91 (12H, t, J=6.8 Hz), 1.38 (24H, s), 1.79 (8H, br s), 2.34 (6H, s), 2.98 (6H, s), 3.31 (8H, m), 4.57 (4H, s), 7.23 (4H, d, J=8.0 Hz), 7.68 (8H, s+d, J=5.6 Hz)

The results of elementary analysis for $C_{48}H_{80}N_2S_2O_6$ will be given below.

|  | C | H | N |
|---|---|---|---|
| Calculated %: | 68.20 | 9.54 | 3.31 |
| Found %: | 67.96 | 9.59 | 3.81 |

These results of analysis show that 4BAMP-6S is the desired compound.

4BAMP-6S was then measured for melting point by DSC. The results were 160.6° C.

The sample 4BAMP-6S obtained in Example 6 was then determined for oral toxicity ($LD_{50}$:rat). The results were greater than 2,000 mg/kg, demonstrating that the product has a low toxicity.

Example 7

The procedure of Example 6 was followed except that, as the tertiary amine, N,N,N',N'-tetraoctyl-p-xylylenediamine was used instead of N,N,N',N'-tetrahexyl-p-xylylenediamine. As a result, 12.58 g of 1,4-bis(N,N-dioctyl-N-methylammoniomethyl)phenylene di-p-toluenesulfonate (abbreviated as "4BAMP-8S") was obtained as the desired compound in the form of white solid compound. The yield of 4BAMP-8S was 66%.

The results of $^1$H-NMR analysis (solvent: $CD_3OD$) of 4BAMP-8S thus obtained will be given below.

0.88 (12H, t, J=6.8 Hz), 1.36 (24H,s), 1.80 (8H, br s), 2.35 (6H, s), 3.02 (6H, s), 3.31 (8H, m), 4.65 (4H, s), 7.23 (4H, d, J=8.0 Hz), 7.72 (8H, s+d, J=6.0 Hz)

The results of elementary analysis for $C_{56}H_{96}N_2S_2O_6$ will be given below.

|  | C | H | N |
|---|---|---|---|
| Calculated %: | 70.25 | 10.11 | 2.93 |
| Found %: | 69.60 | 9.78 | 3.26 |

These results of analysis show that 4BAMP-8S is the desired compound.

Example 8

In a 300 ml reaction vessel were charged 20 mmol of N,N'-dibutyl-N,N'-dimethyl-p-xylylenediamine as a tertiary amine, 120 mmol of hexyl iodide as a quaterizing agent and 100 g of ethanol as a solvent. The reaction mixture was then allowed to undergo reaction by heating under reflux in a nitrogen atmosphere for 10 hours. Ethanol as a solvent was then removed from the reaction product. The reaction product was recrystallized from acetonitrile, and then dried under reduced pressure to obtain 6.86 g of 1,4-bis(N-butyl-N-hexyl-N-methylammoniomethyl)phenylene diiodide (abbreviated as 4BAMP-4,6I) as the desired compound in the form of white compound. The yield of the desired compound was 49%.

The results of $^1$HNMR analysis (solvent: $CD_3OD$) of 4BAMP-4,6I thus obtained will be given below.

0.91 (6H, t, J=7.2 Hz), 1.10 (6H, t, J=7.6 Hz), 1.36 (16H, s), 1.86 (4H, br s), 2.45 (4H, br s), 3.13 (6H, s), 3.32 (4H, m), 3.64 (4H, m), 5.34 (8H, s), 7.75 (4H, s)

The results of elementary analysis for $C_{30}H_{58}N_2I_2$ will be given below.

|  | C | H | N |
|---|---|---|---|
| Calculated %: | 51.43 | 8.34 | 4.00 |
| Found %: | 50.83 | 8.24 | 4.10 |

These results of analysis show that 4BAMP-4,6I is the desired compound.

Example 9

The procedure of Example 8 was followed except that, as the quaterizing agent, octyl iodochloride was used instead of hexyl iodide. As a result, 6.56 g of 1,4-bis(N-butyl-N-octyl-N-methylammoniomethyl)phenylene diiodide (abbreviated as "4BAMP-4,8I") was obtained as the desired compound in the form of white compound. The yield of the desired compound was 43%.

The results of $^1$H-NMR analysis (solvent: $CD_3OD$) of 4BAMP-4,8I thus obtained will be given below.

0.88 (6H, t, J=7.2 Hz), 1.09 (6H, t, J=7.6 Hz), 1.34 (24H, s), 1.84 (4H, br s), 2.44 (4H, br s), 3.13 (6H, s), 3.28 (4H, m), 3.64 (4H, m), 5.30 (8H, s), 7.73 (4H, s)

The results of elementary analysis for $C_{34}H_{66}N_2I_2$ will be given below.

|  | C | H | N |
|---|---|---|---|
| Calculated %: | 53.97 | 8.79 | 3.70 |
| Found %: | 52.84 | 8.63 | 3.90 |

These results of analysis show that 4BAMP-4,8I is the desired compound.

Example 10

In a 300 ml reaction vessel were charged 20 mmol of 3,6-bis(chloromethyl)durene as a halogen compound, 42 mmol of N,N-dibutyl-N-methylamine as a tertiary amine and 100 ml of ethanol as a solvent. The reaction mixture was then allowed to undergo reaction by heating under reflux for 5 hours. Ethanol as a solvent was then removed from the reaction product under reduced pressure to obtain a crude crystal. The crude crystal was recrystallized from solution of acetonitrile and ethyl ether acetate, and then dried under reduced pressure to obtain 3.3 g of 1,4-bis(N,N-butyl-N-methylammoniomethyl)-2,3,5,6-tetramethylphenylene dichloride (abbreviated as "BAMD-4") in the form of white compound. The yield of the desired compound was 32%.

The results of $^1$H-NMR analysis (solvent: $CD_3OD$) of BAMD-4 thus obtained will be given below.

0.92 (12H, t), 1.38 (8H, br s), 1.78 (8H, br s), 2.35 (12H, s), 3.03 (6H, s), 3.48 (8H, m), 5.15 (4H, s)

The results of elementary analysis for $C_{30}H_{58}N_2Cl_2$ will be given below.

|  | C | H | N |
|---|---|---|---|
| Calculated %: | 69.60 | 11.29 | 5.41 |
| Found %: | 69.15 | 11.21 | 5.83 |

From these results of analysis, the product obtained was identified as the desired compound.

Example 11

The procedure of Example 10 was followed except that, as the tertiary amine, N,N-dipentyl-N-methylamine was used instead of N,N-dibutyl-N-methylamine. As a result, 2.4 g of 1,4-bis(N,N-dipentyl-N-methylammoniomethyl)-2,3,5,6-tetramethylphenylene dichloride (abbreviated as "BAMD-5") was obtained as the desired compound in the form of white compound. The yield of the desired compound was 21%.

The results of 1H-NMR analysis (solvent: $CD_3OD$) of BAMD-5 thus obtained will be given below.

0.91 (12H, t), 1.38 (16H, br s), 1.80 (8H, br s), 2.36 (12H, s), 3.03 (6H, s), 3.51 (8H, m), 5.14 (4H, s)

The results of elementary analysis for $C_{34}H_{66}N_2Cl_2$ will be given below.

|  | C | H | N |
|---|---|---|---|
| Calculated %: | 71.17 | 11.59 | 4.88 |
| Found %: | 71.18 | 11.41 | 5.16 |

From these results of analysis, the product obtained was identified as the desired compound.

Example 12

The procedure of Example 10 was followed except that, as the tertiary amine, N,N-dihexyl-N-methylamine was used instead of N,N-dibutyl-N-methylamine. As a result, 4.2 g of 1,4-bis(N,N-dihexyl-N-methylammoniomethyl)-2,3,5,6-tetramethylphenylene dichloride (abbreviated as "BAMD-6") was obtained as the desired compound in the form of white compound. The yield of the desired compound was 33%.

The results of $^1$H-NMR analysis (solvent: $CD_3OD$) of BAMD-6 thus obtained will be given below.

0.91 (12H, t), 1.38 (24H, br s), 1.79 (8H, br s), 2.35 (12H, s), 3.03 (6H, s), 3.49 (8H, m), 5.16 (4H, s)

The results of elementary analysis for $C_{38}H_{74}N_2Cl_2$ will be given below.

|  | C | H | N |
|---|---|---|---|
| Calculated %: | 72.46 | 11.84 | 4.45 |
| Found %: | 72.38 | 11.71 | 4.76 |

From these results of analysis, the product obtained was identified as the desired compound.

The sample BAND-6 thus obtained was then determined for oral toxicity ($LD_{50}$: rat). The results were greater than 2,000 mg/kg.

Example 13

The procedure of Example 10 was followed except that, as the tertiary amine, N,N-octyl-N-hexyl-N-methylamine was used instead of N,N-dibutyl-N-methylamine. As a result, 2.3 g of 1,4-bis(N-octyl-N-hexyl-N-methylammoniomethyl)-2,3,5,6-tetramethylphenylene dichloride (abbreviated as "BAMD-6,8") was obtained as the desired compound in the form of white compound. The yield of the desired compound was 17%.

The results of $^1$H-NMR analysis (solvent: $CD_3OD$) of BAMD-6,8 thus obtained will be given below.

0.93 (12H, t), 1.39 (32H, br s), 1.80 (8H, br s), 2.37 (12H, s), 3.06 (6H, s), 3.52 (8H, m), 5.19 (4H, s)

The results of elementary analysis for $C_{42}H_{82}N_2Cl_2$ will be given below.

|  | C | H | N |
|---|---|---|---|
| Calculated %: | 73.53 | 12.05 | 4.08 |
| Found %: | 73.38 | 12.01 | 4.46 |

From these results of analysis, the product obtained was identified as the desired compound.

Example 14

The procedure of Example 10 was followed except that, as the tertiary amine, N,N-dioctyl-N-methylamine was used instead of N,N-dibutyl-N-methylamine. As a result, 2.0 g of 1,4-bis(N,N-dioctyl-N-methylammoniomethyl)-2,3,5,6-tetramethylphenylene dichloride (abbreviated as "BAMD-8") was obtained as the desired compound in the form of white compound. The yield of the desired compound was 14%.

The results of $^1$H-NMR analysis (solvent: $CD_3OD$) of BAMD-8 thus obtained will be given below.

0.92 (12H, t), 1.38 (40H, br s), 1.81 (8H, br s), 2.38 (12H, s), 3.05 (6H, s), 3.54 (8H, m), 5.18 (4H, s)

The results of elementary analysis for $C_{46}H_{90}N_2Cl_2$ will be given below.

|  | C | H | N |
|---|---|---|---|
| Calculated %: | 74.45 | 12.22 | 3.78 |
| Found %: | 74.35 | 12.01 | 4.06 |

From these results of analysis, the product obtained was identified as the desired compound.

Example 15

The procedure of Example 10 was followed except that, as the halogen compound, 2,4-bis(chloromethyl)-1,3,5-trimethylbenzene was used instead of 1,4-bis(chloromethyl)durene. As a result, 0.7 g of 2,4-bis(N,N-dibutyl-N-methylammoniomethyl)-1,3,5-trimethylbenzene dichloride (abbreviated as "BAMT-4") as the desired compound in the form of white compound. The yield of the desired compound was 7%.

The results of $^1$H-NMR analysis (solvent: $CD_3OD$) of BAMT-4 thus obtained will be given below.

0.91 (12H, t), 1.38 (8H, br s), 1.79 (8H, br s), 2.35 (9H, s), 3.03 (6H, s), 3.49 (8H, m), 5.16 (4H, s), 6.82 (1H, s)

The results of elementary analysis for $C_{29}H_{56}N_2Cl_2$ will be given below.

|  | C | H | N |
|---|---|---|---|
| Calculated %: | 69.15 | 11.21 | 5.56 |
| Found %: | 69.10 | 11.11 | 5.79 |

These results of analysis show that BAMT-4 is the desired compound.

Example 16

The procedure of Example 15 was followed except that, as the tertiary amine, N,N-dipentyl-N-methylamine was used instead of N,N-dibutyl-N-methylamine. As a result, 0.8 g of 2,4-bis(N,N-dipentyl-N-methylammoniomethyl)-1,3,5-trimethylbenzene dichloride (abbreviated as "BAMT-5") was obtained as the desired compound in the form of white compound. The yield of the desired compound was 7%.

The results of $^1$H-NMR analysis (solvent: CD$_3$OD) of BAMT-5 thus obtained will be given below.

0.90 (12H, t), 1.36 (16H, br s), 1.78 (8H, br s), 2.35 (9H, s), 3.05 (6H, s), 3.47 (8H, m), 5.14 (4H, s), 6.82 (1H, s)

The results of elementary analysis for $C_{33}H_{64}N_2Cl_2$ will be given below.

|  | C | H | N |
|---|---|---|---|
| Calculated %: | 70.86 | 11.52 | 5.00 |
| Found %: | 70.68 | 11.41 | 5.26 |

From these results of analysis, the product obtained was identified as the desired compound.

Example 17

The procedure of Example 15 was followed except that, as the tertiary amine, N,N-dihexyl-N-methylamine was used instead of N,N-dibutyl-N-methylamine. As a result, 1.4 g of 2,4-bis(N,N-dihexyl-N-methylammoniomethyl)-1,3,5-trimethylbenzene dichloride (abbreviated as "BAMT-6") was obtained as the desired compound in the form of white compound. The yield of the desired compound was 11%.

The results of $^1$H-NMR analysis (solvent: CD$_3$OD) of BAMT-6 thus obtained will be given below.

0.91 (12H, t), 1.38 (24H, br s), 1.79 (8H, br s), 2.35 (9H, s), 3.03 (6H, s), 3.49 (8H, m), 5.16 (4H, s), 6.81 (1H, s)

The results of elementary analysis for $C_{37}H_{72}N_2Cl_2$ will be given below.

|  | C | H | N |
|---|---|---|---|
| Calculated %: | 72.16 | 11.78 | 4.55 |
| Found %: | 72.18 | 11.71 | 4.76 |

From these results of analysis, the product obtained was identified as the desired compound.

Example 18

The procedure of Example 15 was followed except that, as the tertiary amine, N-octyl-N-hexyl-N-methylamine was used instead of N,N-dibutyl-N-methylamine. As a result, 1.1 g of 2,4-bis(N-octyl-N-hexyl-N-methylammoniomethyl)-1,3,5-trimethylbenzene dichloride (abbreviated as "BAMT-6, 8") was obtained as the desired compound in the form of white compound. The yield of the desired compound was 8%.

The results of $^1$H-NMR analysis (solvent: CD$_3$OD) of BAMT-6,8 thus obtained will be given below.

0.92 (12H, t), 1.39 (32H, br s), 1.79 (8H, br s), 2.37 (9H, s), 3.06 (6H, s), 3.51 (8H, m), 5.18 (4H, s), 6.84 (1H, s)

The results of elementary analysis for $C_{41}H_{80}N_2Cl_2$ will be given below.

|  | C | H | N |
|---|---|---|---|
| Calculated %: | 73.28 | 12.00 | 4.17 |
| Found %: | 73.18 | 11.85 | 4.36 |

From these results of analysis, the product obtained was identified as the desired compound.

Example 19

The procedure of Example 15 was followed except that, as the tertiary amine, N,N-dioctyl-N-methylamine was used instead of N,N-dibutyl-N-methylamine. As a result, 1.2 g of 2,4-bis(N,N-dioctyl-N-methylammoniomethyl)-1,3,5-trimethylbenzene dichloride (abbreviated as "BAMT-8") was obtained as the desired compound in the form of white compound. The yield of the desired compound was 8%.

The results of $^1$H-NMR analysis (solvent: CD$_3$OD) of BAMT-8 thus obtained will be given below.

0.93 (12H, t), 1.40 (40H, br s), 1.80 (8H, br s), 2.36 (9H, s), 3.04 (6H, s), 3.51 (8H, m), 5.19 (4H, s), 6.85 (1H, s)

The results of elementary analysis for $C_{45}H_{88}N_2Cl_2$ will be given below.

|  | C | H | N |
|---|---|---|---|
| Calculated %: | 74.23 | 12.18 | 3.85 |
| Found %: | 74.11 | 12.02 | 4.06 |

From these results of analysis, the product obtained was identified as the desired compound.

G-2. TEST EXAMPLES

Examples of test on the antimicrobial properties and anti-septic properties of compounds of the invention will be given below. For comparison, 4 kinds of conventional antimicrobial agents were prepared.

Comparative Example 1

As Comparative Example 1, benzalkonium chloride, which is a commercially available quaternary ammonium salt-based antimicrobial agent, was prepared.

Comparative Example 2

As Comparative Example 2, an antimicrobial agent proposed in JP-A-10-114604 was prepared as follows. In a 300 ml reaction vessel were charged 20 mmol of α,α'-dichlorop-xylene as a halogen compound, 42 mmol of N-dodecyl-N,N-dimethylamine as a tertiary amine and 100 ml of ethanol as a solvent. The reaction mixture was then allowed to undergo reaction by heating under reflux for 5 hours. Ethanol as a solvent was then removed from the reaction product under reduced pressure to obtain a crude crystal. The crude crystal was recrystallized from diethyl ether, and then dried under reduced pressure to obtain 8.02 g of 1,4-bis(N-dodecyl-N,N-dimethylammoniomethyl) phenylene dichloride (abbreviated as "4BADMP-12C") in the form of white compound. The yield of the desired compound was 70%.

The results of $^1$H-NMR analysis (solvent: $CD_3OD$) of 4BADMP-12C thus obtained will be given below.

0.93 (6H, t, J=6.8 Hz), 1.30 (36H, br), 1.85 (4H, br s), 3.25 (12H, s), 3.60 (4H, m), 5.30 (4H, s), 7.85 (4H, s)

The results of elementary analysis for $C_{36}H_{70}N_2Cl_2$ will be given below.

|  | C | H | N |
|---|---|---|---|
| Calculated %: | 71.84 | 11.72 | 4.65 |
| Found %: | 71.51 | 11.48 | 5.03 |

These results of analysis show that 4BADMP-12C is the desired compound.

Comparative Example 3

As Comparative Example 3, an antimicrobial agent proposed in JP-A-6-321902 was prepared as follows. 20 mmol of 4-mercaptopyridine was dissolved in 50 ml of ethanol. To the solution was then added dropwise 10 mmol of 1,6-dibromohexane with stirring. Subsequently, the reaction mixture was allowed to undergo reaction by heating under reflux for 12 hours. The solution was then allowed to cool. The resulting white precipitate was then withdrawn by filtration. The precipitate thus obtained was then dissolved in 50 ml of water. To the solution was then added dropwise a 1N NaOH aqueous solution until the pH value of the solution reached 11. The solution was then extracted with diethyl ether three times. A molecular sieve 3A 1/16 (produced by Wako Pure Chemical Industries, Ltd.) was put in the resulting ether phase. The ether phase was dried overnight. Ether was then removed from the material. As a result, a light yellow liquid compound was obtained. To this compound was then added 50 ml of DMF to make a solution. To this solution was then added 40 mmol of octyl iodide. The reaction mixture was then allowed to undergo reaction by heating under reflux for 24 hours. After the termination of reaction, DMF as a solvent was then removed. The resulting light yellow solid was recrystallized from acetonitrile, and then dried under reduced pressure to obtain 4.40 g of 4,4'-(1,6-dithiohexamethylene)-bis-(1-octylpyridinium iodide) (abbreviated as "4MHO") in the form of white solid compound. The yield of the desired compound was 56%.

The results of $^1$H-NMR analysis (solvent: $CD_3OD$) of 4MHO thus obtained will be given below.

0.81 (6H, t, J=7.2 Hz), 1.25 (20H, m), 1.71 (8H, m), 3.32 (8H, m), 4.78 (4H, m), 7.80 (8H, m)

The results of elementary analysis for $C_{32}H_{54}N_2S_2I_6$ will be given below.

|  | C | H | N |
|---|---|---|---|
| Calculated %: | 48.98 | 6.94 | 3.57 |
| Found %: | 48.77 | 6.75 | 3.95 |

Comparative Example 4

As Comparative Example 4, an antimicrobial agent proposed in JP-A-2000-95763 was prepared as follows. 20 mmol of 4-mercaptopyridine was dissolved in 50 ml of acetone. To the solution was then added dropwise 10 mmol of xylylene dichloride with stirring. Subsequently, the reaction mixture was allowed to undergo reaction by heating under reflux for 5 hours. The solution was then allowed to cool. The resulting white precipitate was then withdrawn by filtration. The precipitate thus obtained was washed with acetone, and then dissolved in 50 ml of water. To the solution was then added dropwise a 0.5N NaOH aqueous solution until the pH value of the solution reached 10. The solution was then extracted with toluene three times. The resulting organic phase was washed with water, and then dried. Toluene was then removed from the material under reduced pressure to obtain a crude crystal. To the crude crystal was then added 50 ml of DMF. To the mixture was then added 40 mmol of octyl iodide. The reaction mixture was then allowed to undergo reaction at a temperature of 100° C. After the termination of reaction, DMF as a solvent was then removed. The resulting light yellow solid was put into 200 ml of ethyl ester acetate. The resulting solid was withdrawn by filtration, recrystallized from a mixture of acetonitrile and ethyl ester acetate, and then dried under reduced pressure to obtain 4.0 g of 4,4'-(p-xylyldithio)-bis(1-octylpyridinium iodide) (abbreviated as "I-8") in the form of white solid compound (yield: 50%).

G-2-1. Minimum Bactericidal Concentration (MBC) Against Bacteria

Test Example 1

A bacteria solution in the initial stage of logarithmic productive phase which had been adjusted with a nutrient broth according to an ordinary sterilized water dilution method such that the concentration of bacterial suspension reached $10^6$ cell/ml was brought into contact with chemical solutions having concentrations which vary stepwise at a temperature of 30° C. for 30 minutes, and then transplanted to a nutrient broth where it was then allowed to stand at a temperature of 37° C. for 24 hours for culture. The nutrient broth was then examined to see if the proliferation of bacteria occurred. Thus, MBC was determined.

Five kinds of gram-negative bacteria and four kinds of gram-positive bacteria were used as sample bacteria.

4BAMP-6C (Example 1), 4BAMP-6S (Example 6), and benzalkonium chloride (Comparative Example 1) were used as test samples. The results are set forth in Table 1 below.

TABLE 1

| Sample bacteria | MBC (ppm) | | |
|---|---|---|---|
| | 4BAMP-6C | 4BAMP-6S | Benzalkonium chloride |
| *Pseudomonas aeruginosa* ATCC 27583 | 16 | 8 | 32 |
| *Klebsiella pneumoniae* ATCC 13883 | <2 | <2 | 8 |
| *Proteus rettgeri* NIT 96 | <2 | <2 | 16 |
| *Escherichia coli* K12 OUT 8401 | 8 | 4 | 8 |
| *Escherichia coli* K12 W 3110 | 16 | 8 | 16 |
| *Bacillus subtilis* IFO 3134 | <2 | <2 | 4 |
| *Bacillus substilis* ATCC 6633 | <2 | <2 | 4 |
| *Bacillus cereus* ISO 3001 | 4 | 4 | 4 |
| *Staphylococcus aureus* ISO 12732 | <2 | <2 | <2 |

Test Example 2

BAMP-6 (Example 12), BAMD-6,8 (Example 13), BAMT-6 (Example 17) and benzalkonium chloride (Comparative Example 1) were determined for MBC value against 5 kinds of gram-negative bacteria and 4 kinds of gram-positive bacteria in the same manner as in Test Example 1. The results are set forth in Table 2 below.

TABLE 2

| Sample bacteria | MBC (ppm) | | | |
|---|---|---|---|---|
| | BAMD-6 | BAMD-6, 8 | BAMT-6 | Benzalkonium chloride |
| *Pseudomonas aeruginosa* ATCC 27583 | 4 | <2 | 4 | 32 |
| *Klebsiella pneunoniae* ATCC 13883 | <2 | <2 | <2 | 8 |
| *Proteus rettgeri* NIT 96 | <2 | <2 | <2 | 16 |
| *Escherichia coli* K12 OUT 8401 | <2 | <2 | <2 | 8 |
| *Escherichla coli* K12 W 3110 | 4 | <2 | 4 | 16 |
| *Bacillus subtilis* IFO 3134 | <2 | <2 | <2 | 4 |
| *Bacillus substilis* ATCC 6633 | <2 | <2 | <2 | 4 |
| *Bacillus cereus* IFO 3001 | <2 | <2 | <2 | 4 |
| *Staphylococcus aureus* IFO 12732 | <2 | <2 | <2 | <2 |

G-2-2. Minimum Development Inhibiting Concentration (MIC) Against Bacteria

Test Example 3

A bacteria solution in stationary state which had been adjusted with a nutrient broth according to an ordinary broth dilution method such that the concentration of bacterial suspension reached $10^6$ cell/ml was added to chemical solutions having concentrations which vary stepwise where it was then allowed to stand at a temperature of 37° C. for 24 hours for culture. The bacteria solution was then examined to see if the proliferation of bacteria occurred. Thus, MIC was determined.

*Escherichia coli* K12 W 3110 was used as a sample bacterium. Compounds obtained in Examples 1 to 9 and benzalkonium chloride prepared in Comparative Example 1 were used as test samples. The results are set forth in Table 3 below.

TABLE 3

| Example No./ Comparative Example No. | Kind of bis quaternary ammonium salt | MIC (ppm) *Escherichia coli* K12 W 3110 |
|---|---|---|
| Example 1 | 4BAMP-6C | 2 |
| Example 2 | 4BAMP-8C | 1 |
| Example 3 | 3BAMP-6C | 1 |
| Example 4 | 2BAMP-6C | 1 |
| Example 5 | 4BAMP-5S | 16 |
| Example 6 | 4BAMP-6S | 2 |
| Example 7 | 4BAMP-8S | 1 |
| Example 8 | 4BAMP-4, 6I | 16 |
| Example 9 | 4BAMP-4, 8I | 2 |
| Comparative Example 1 | Benzalkonium chloride | 8 |

Test Example 4

The compounds obtained in Examples 10 to 19 and benzalkonium chloride were determined for MIC value against *Escherichia coli* K12 W 3110 in the same manner as in Test Example 3. The results are set forth in Table 4 below.

TABLE 4

| Example No. | Kind of bis quaternary ammonium salt | MIC (ppm) *Escherichia coli* K12 W 3110 |
|---|---|---|
| Example 10 | BAMD-4 | 16 |
| Example 11 | BAMD-5 | 2 |
| Example 12 | BAMD-6 | 1 |
| Example 13 | BAMD-6, 8 | 1 |
| Example 14 | BAMD-8 | 1 |
| Example 15 | BAMT-4 | 8 |
| Example 16 | BAMT-5 | 2 |
| Example 17 | BAMT-6 | 1 |
| Example 18 | BAMT-6, 8 | 1 |
| Example 19 | BAMT-8 | 1 |
| Comparative Example 1 | Benzalkonium chloride | 8 |

Test Example 5

MIC value was determined by an agar plate dilution method according to the Law of Japanese Society of Chemotherapy. In some detail, a bacteria solution in stationary state which had been adjusted with a nutrient broth such that the concentration of bacterial suspension reached $10^6$ cell/ml was added to agar culture media containing chemical solutions having concentrations which vary in two stages where it was then allowed to stand at a temperature of 37° C. for 24 hours for culture. The bacteria solution was then examined to see if the proliferation of bacteria occurred. Thus, MIC was determined.

The following three kinds of bacteria were used as sample bacteria:

*Escherichia coli* K12 W 3110 (*E. coli*);

*Pseudomonas aeruginosa* $ATCC_{27583}$ (*P. auruginosa*); and

*Staphylococcus aureus* IFO 12732 (*S. aureus*)

4BAMP-5C (1,4-bis(N,N-dipentyl-N-methylammoniomethyl)phenylene dichloride), 4BAMP-6C (Example 1), 4BAMP-6,8B (1,4-bis(N-octyl-N-hexyl-N-methylammoniomethyl)phenylene dibromide) and benzalkonium chloride (Comparative Example 1) were used as test samples. The results are set forth in Table 5 below.

TABLE 5

| | MIC (ppm) | | | |
|---|---|---|---|---|
| Sample bacteria | 4BAMP -5C | 4BAMP -6C | 4BAMP -6, 8B | Benzalkonium chloride |
| E. coli | 16 | 8 | 8 | 32 |
| P. aeruginosa | 4 | <2 | <2 | 8 |
| S. aureus | <2 | <2 | <2 | 16 |

As can be seen in the results of Test Examples 1 to 5, MBC value or MIC value of the compounds of the invention are equal to or smaller than that of benzalkonium chloride, demonstrating that the compounds of the invention have an antimicrobial power equal to or higher than that of benzalkonium chloride.

G-2-3. Minimum Development Inhibiting Concentration (MIC) against the Fungi

Test Example 6

A sample fungus which had been pre-cultured was diluted with a wetting agent-containing sterilized water according to an ordinary broth dilution method to prepare a spore solution. 1 ml of the spore solution was then mixed with 1 ml of each of chemical solutions having concentrations which vary stepwise. The mixture was then cultured at a temperature of 27° C. in an incubator for 1 week. The culture was then examined for turbidity to see if the proliferation of fungus occurred. The minimum concentration at which no turbidity occurs was defined to be MIC.

*Aspergillus niger* IFO 6431 (*A. niger*) and *Candida albicans* $ATCC_{10231}$ (*C. albicans*) were used as sample microorganisms.

4BAMP-5C (1,4-bis(N,N-dipentyl-N-methylammoniomethyl)phenylene dichloride), 4BAMP-6C (Example 1), 4BAMP-6,8B (1,4-bis(N-octyl-N-hexyl-N-methylammoniomethyl)phenylene dibromide) and benzalkonium chloride (Comparative Example 1) were used as test samples. The results are set forth in Table 6 below.

TABLE 6

| | MIC (ppm) | | | |
|---|---|---|---|---|
| Sample fungus | 4BAMP -5C | 4BAMP -6C | 4BAMP -6, 8B | Benzalkonium chloride |
| A. niger | 16 | 16 | 8 | 32 |
| C. albicans | 8 | 4 | <2 | 16 |

As can be seen in the results of Test Example 6, MIC value of the compounds of the invention is smaller than that of benzalkonium chloride, demonstrating that the compounds of the invention have a higher antifungal power than that of benzalkonium chloride.

G-2-4. Minimum Hemolytic Activity Concentration Against Erythrocyte

Test Example 7

Human blood was collected. The sample blood was then mixed with the equal amount of alsebar solution (glucose: 2.05 g; NaCl: 0.42 g; sodium citrate: 0.8 g; citric acid: 0.55 g; pH: 6.1). The mixture was then stored at a temperature of 4° C. Shortly before used for experiment, the alsebar stored blood was subjected to centrifugal separation. Thus, the supernatant liquid and the leukocyte layer on the erythrocyte were removed. To the erythrocyte was then added PBS in an amount of about 10 times that of the erythrocyte to obtain a 50% erythrocyte. 10 μl of the 50% erythrocyte was then mixed with 990 μl of each of chemicals which had been diluted with PBS in amounts varying stepwise. The erythrocyte was acted upon by the chemical at a temperature of 37° C. for 1 hour. The mixture was then subjected to centrifugal separation. The supernatant liquid was collected for the measurement of the optical density at 540 nm (O.D.540). Separately, the foregoing procedure was followed except that no chemicals were used to prepare a 0% hemolytic control. The foregoing procedure was followed except that Milliq water was used instead of PBS to prepare a 100% hemolytic control. For the minimum hemolytic activity concentration of chemical, the minimum concentration at which the hemolytic concentration is not higher than 50% was determined.

4BAMP-6C (Example 1), 4BAMP-5S (Example 5), 4BAMP-6S (Example 6), benzalkonium chloride (Comparative Example 1), 4BADMP-12C (Comparative Example 2) and 4MHO (Comparative Example 3) were used as test samples. The results are set forth in Table 7 below.

Table 7 also shows the results of 4BAMP-5C (1,4-bis (N,N-dipentyl-N-methylammoniomethyl)phenylene dichloride) synthesized in the same manner as in Example 1 as a compound of the invention.

TABLE 7

| Test sample | Minimum hemolytic activity concentration (ppm) Erythrocyte |
|---|---|
| 4BAMP-5C | 1,600 |
| 4BAMP-6C | 400 |
| 4BAMP-5S | 400 |
| 4BAMP-6S | 400 |
| Benzalkonium chloride | 25 |
| 4BADMP-12C | 12.5 |
| 4MHO | 25 |

Test Example 8

BAND-5 (Example 11), BAND-6 (Example 12), BAMT-5 (Example 16), BAMT-6 (Example 17), benzalkonium chloride (Comparative Example 1), 4BADNP-12C (Comparative Example 2), 4MHO (Comparative Example 3) and I-8 (Comparative Example 4) were measured for minimum hemolytic activity concentration in the same manner as in Test Example 5. The results are set forth in Table 8 below.

TABLE 8

| Test sample | Minimum hemolytic activity concentration (ppm) Erythrocyte |
|---|---|
| BAMD-5 | 800 |
| BAMD-6 | 400 |
| BAMT-5 | 800 |
| BAMT-6 | 400 |
| Benzalkonium chloride | 25 |
| 4BADMP-12C | 12.5 |
| 4MHO | 25 |
| I-8 | 50 |

As can be seen in the results of Test Examples 7 and 8, the compounds of the invention exhibit a minimum hemolytic activity concentration of about 8 to 60 times greater than that of the conventional antimicrobial agents, demonstrating that the compounds of the invention are remarkably superior to the conventional antimicrobial agents in respect to safety to human.

G-2-5. Interaction with Eye Drop Components

Test Example 9

Eye drop components and the preservative of the invention were dissolved in a 1% sodium chloride solution. The solution was then neutralized with a proper amount of diluted hydrochloric acid or sodium hydroxide. The neutralized solution thus obtained was then visually observed for transparency.

Chondroitin sodium sulfate (hereinafter abbreviated as "SKA"), sodium hyaluronate (hereinafter abbreviated as "SHA"), sodium cromoglicate (hereinafter abbreviated as "SCA"), sodium dimethylisopropylazulenesulfonate (hereinafter abbreviated as "SDPA"), and flavin-adenine dinucleotide (hereinafter abbreviated as "FA") were used as the eye drop components. 4BAMP-6C (Example 1) and benzalkonium chloride (Comparative Example 1) were used as test samples of preservative.

The mixing ratio and the results of observation are set forth in Table 9.

The solutions comprising the preservatives of the invention incorporated therein were transparent while the solutions comprising benzalkonium chloride incorporated therein were slightly opaque.

TABLE 9

| Compound | Mixing ratio | 4BAMP-6C | Benzalkonium chloride | Results |
|---|---|---|---|---|
| SKA | 3% | 0.1% | — | Transparent |
|  | 3% | — | 0.01% | Clouded |
| SHA | 0.2% | 0.1% | — | Transparent |
|  | 0.2% | — | 0.01% | Clouded |
| SCA | 3% | 0.1% | — | Transparent |
|  | 3% | — | 0.01% | Clouded |
| SDPA | 0.05% | 0.1% | — | Transparent |
|  | 0.05% | — | 0.01% | Clouded |
| FA | 0.1% | 0.1% | — | Transparent |
|  | 0.1% | — | 0.01% | Clouded |

G-2-6. Anti-septic Power Test

Test Example 10

Solutions prepared according to the formulation set forth in Tables 10 and 11 below were subjected to anti-septic power test according to the method defined in *Pharmacopoeia of the United States XX*, 873 (1980). The solutions thus tested were then observed for anti-septic power after 1 hour, 4 hours, 24 hours, 7 days, 14 days, 21 days and 28 days. As test microorganisms, *E. coli, P. auru.* and *S. Aureus* were used as bacteria and *A. niger* and *C. albicans* were used as fungi. 4BAMP-6C and benzalkonium chloride were used as test samples. The results of the time at which the desired anti-septic effect was confirmed are set forth in Table 12 below.

As can be seen in these test results, the preservatives of the invention exhibit anti-septic power in a short period of time, i.e., high anti-septic power as compared with benzalkonium chloride.

TABLE 10

Formulation 1

| Component | wt % |
|---|---|
| Chondroitin sodium sulfate | 1 |
| Sodium chloride | 0.2 |
| Sodium dihydrogenphosphate | 0.02 |
| Disodium hydrogenphosphate | 0.01 |
| Test sample | 0.002 |
| Purified water | Balance |

TABLE 11

Formulation 2

| Component | wt % |
|---|---|
| Taurin | 1 |
| Sodium chloride | 0.2 |

TABLE 11-continued

Formulation 2

| Component | wt % |
|---|---|
| Sodium dihydrogenphosphate | 0.02 |
| Disodium hydrogenphosphate | 0.01 |
| Test sample | 0.002 |
| Purified water | Balance |

TABLE 12

| | Formulation 1 | | Formulation 2 | |
|---|---|---|---|---|
| Sample micro-organism | 4BAMP-6C | Benzalkonium chloride | 4BAMP-6C | Benzalkonium chloride |
| E. coli | 1 hr. | 24 hrs. | 1 hr. | 24 hrs. |
| P. aeruginosa | 1 hr. | 24 hrs. | 1 hr. | 24 hrs. |
| S. aureus | 1 hr. | 4 hrs. | 1 hr. | 4 hrs. |
| A. niger | 7 days | 28 days | 14 days | 28 days |
| C. albicans | 7 days | 21 days | 7 days | 21 days |

While the invention has been described in detail and with reference to specific embodiments thereof, it will be apparent to one skilled in the art that various changes and modifications can be made therein without departing from the spirit and scope thereof.

This application is based on Japanese patent applications No. 2000-141352 filed on May 15, 2000 and No. 2001-26173 filed on Feb. 1, 2001, the entire contents thereof being hereby incorporated by reference.

What is claimed is:

1. A quaternary ammonium salt represented by the following general formula (1):

$$\left[R_2-\overset{R_1}{\underset{R_3}{\overset{\oplus}{N}}}-H_2C-\underset{}{\overset{(CH_3)_k}{\bigcirc}}-CH_2-\overset{R_1}{\underset{R_3}{\overset{\oplus}{N}}}-R_2\right][X^{n-}]_m \quad (1)$$

wherein $R_1$ and $R_2$ each represent a $C_{4-12}$ alkyl group and may be the same or different; $R_3$ represents a $C_{1-2}$ alkyl group; k represents an integer of from 0 to 4; X represents an inorganic or organic anion group; n represents the valence of the anion group X which is selected from 1 and 2; and m represents an integer of 2 when n is 1 or 1 when n is 2.

2. The quaternary ammonium salt according to claim 1, wherein said $R_1$ and $R_2$ each represent a $C_{5-10}$ alkyl group and may be the same or different.

3. The quaternary ammonium salt according to claim 1, wherein said $R_1$ and $R_2$ each represent a $C_{6-8}$ alkyl group and may be the same or different.

4. The quaternary ammonium salt according to claim 1, wherein said inorganic or organic anion group X is selected from the group consisting of an iodine ion, bromine ion, chlorine ion, iodic acid ion, bromic acid ion, chloric acid ion, periodic acid ion, perchloric acid ion, chlorous acid ion, hypochlorous acid ion, nitric acid ion, nitrous acid ion, sulfuric acid ion, hydroxyl group ion, and an anion group represented by any one of the following general formulae (2) to (5):

$$[R_4COO^{\ominus}] \quad (2)$$

wherein $R_4$ represents a $C_{1-7}$ alkyl or alkenyl group which may have hydroxyl group or carbonyl group;

$$[{}^{\ominus}OCO-R_5-COO^{\ominus}] \quad (3)$$

wherein $R_5$ does not exist (the two groups COO are directly bonded to each other) or represents a $C_{1-8}$ alkyl or alkenyl group which may have hydroxyl group;

$$[R_6SO_4^{\ominus}] \quad (4)$$

wherein $R_6$ represents a $C_{1-2}$ alkyl group; and $$\left[\underset{R_8}{\overset{R_7}{\bigcirc}}-SO_3^{\ominus}\right] \quad (5)$$

wherein $R_7$ and $R_8$ each represent a hydrogen atom, $C_{1-2}$ alkyl group or carboxyl group.

5. A process for the preparation of a quaternary ammonium salt of claim 1 which comprises reacting a compound represented by the following general formula (6) with a compound represented by the following general formula (7):

$$Y-H_2C-\underset{}{\overset{(CH_3)_k}{\bigcirc}}-CH_2-Y \quad (6)$$

wherein k represents an integer of from 0 to 4; and Y represents a chlorine atom, bromine atom or iodine atom; and $$R_1-\overset{R_3}{\underset{}{N}}-R_2 \quad (7)$$

wherein $R_1$ and $R_2$ each represent a $C_{4-12}$ alkyl group; and $R_3$ represents a $C_{1-2}$ alkyl group.

6. A process for the preparation of a quaternary ammonium salt of claim 1, which comprises reacting a compound represented by the following general formula (8) with a compound represented by the following general formula (9):

$$R_2-\overset{R_1}{\underset{}{N}}-H_2C-\underset{}{\overset{(CH_3)_k}{\bigcirc}}-CH_2-\overset{R_1}{\underset{}{N}}-R_2 \quad (8)$$

wherein $R_1$ and $R_2$ may be the same or different and each represent a $C_{4-12}$ alkyl group; and k represents an integer of from 0 to 4; and $$R_3-Z \quad (9)$$

wherein $R_3$ represents a $C_{1-2}$ alkyl group; and Z represents a chlorine atom, bromine atom, iodine atom or a group represented by any one of the following general formulae (10) and (11):

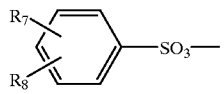
(10)

wherein $R_6$ represents a $C_{1-2}$ alkyl group; and

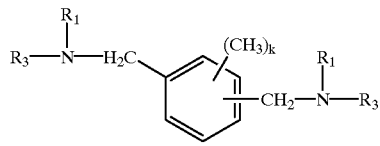
(11)

wherein $R_7$ and $R_8$ each represent a hydrogen atom, $C_{1-12}$ alkyl group or carboxyl group.

7. A process for the preparation of a quaternary ammonium salt of claim 1 which comprises reacting a compound represented by the following general formula (12) with a compound represented by the following general formula (13):

(12)

$R_2$—J  (13)

wherein $R_1$ represents a $C_{4-12}$ alkyl group; $R_3$ represents a $C_{1-2}$ alkyl group; and k represents an integer of from 0 to 4; and wherein $R_2$ represents a $C_{4-12}$ alkyl group; and J represents a chlorine atom, bromine atom, iodine atom or a group represented by the general formula (11).

8. A process for the preparation of a quaternary ammonium salt which comprises substituting the anion group in the quaternary ammonium salt having a cation group of the following general formula (14) prepared by the preparation process according to any one of claims 3 to 5, with an anion group selected from the group consisting of iodine ion, bromine ion, chlorine ion, iodic acid ion, bromic acid ion, chloric acid ion, periodic acid ion, perchloric acid ion, chlorous acid ion, hypochlorous acid ion, nitric acid ion, nitrous acid ion, sulfuric acid ion, hydroxyl group ion or an anion group represented by any one of the general formulae (2) to (5) according to claim 4,

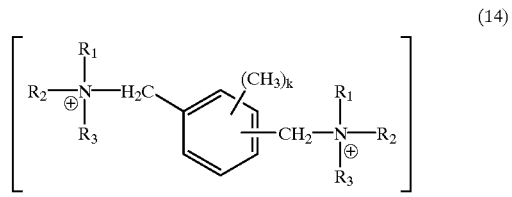
(14)

wherein $R_1$ and $R_2$ each represent a $C_{4-12}$ alkyl group and may be the same or different; $R_3$ represents a $C_{1-2}$ alkyl group; and k represents an integer of from 0 to 4.

9. An antimicrobial agent, comprising as an effective ingredient a quaternary ammonium salt according to claim 1 or 2.

10. A preservative for eye drop, comprising as an effective ingredient a quaternary ammonium salt according to claim 1 or 2.

11. An eye drop comprising as a preservative a quaternary ammonium salt according to claim 1 or 2.

* * * * *